(12) United States Patent
Sullivan et al.

(10) Patent No.: US 6,803,202 B2
(45) Date of Patent: Oct. 12, 2004

(54) COMBINATIONAL STRATEGY FOR IDENTIFICATION OF BIOLOGICAL AGENTS

(75) Inventors: Brian M. Sullivan, Redondo Beach, CA (US); Denes L. Zsolnay, Rolling Hills Estates, CA (US)

(73) Assignee: Northrop Grumman Corporation, Los Angeles, CA (US)

( * ) Notice: Subject to any disclaimer, the term of this patent is extended or adjusted under 35 U.S.C. 154(b) by 413 days.

(21) Appl. No.: 10/055,318

(22) Filed: Oct. 23, 2001

(65) Prior Publication Data

US 2003/0104503 A1 Jun. 5, 2003

(51) Int. Cl.$^7$ ............................................. G01N 33/543
(52) U.S. Cl. ...................... 435/7.92; 435/7.1; 435/7.93; 435/7.94; 436/518
(58) Field of Search ................................. 435/7.1, 7.92, 435/7.93, 7.94, 973; 436/518, 524, 525, 164, 824

(56) References Cited

U.S. PATENT DOCUMENTS

| 5,981,180 A | * | 11/1999 | Chandler et al. ............... 435/6 |
| 6,023,540 A | * | 2/2000 | Walt et al. ...................... 385/12 |
| 6,680,206 B1 | * | 1/2004 | McDevitt et al. ........... 436/172 |
| 2002/0058273 A1 | * | 5/2002 | Shipwash ....................... 435/6 |
| 2003/0077642 A1 | * | 4/2003 | Fritsch et al. ................... 435/6 |

FOREIGN PATENT DOCUMENTS

| GB | WO 99/07879 | * | 2/1999 | ............ C12Q/1/00 |

* cited by examiner

*Primary Examiner*—Long V. Le
*Assistant Examiner*—Gary W. Counts
(74) *Attorney, Agent, or Firm*—Ronald M. Goldman (57) ABSTRACT

The existence of any one of a plurality of $2^N-1$ bioagents in a sample (1) may be determined by dividing the sample into N parts and performing separate ELISA processes (TEST 1 & TEST 2) on each of the N parts concurrently, where N is an integer greater than 1, each of the separate ELISA processes possessing the capability to identify a bioagent from a combination of possible bioagents (3), and in which the combination of possible bioagents of any one of the separate ELISA processes is different (7) from the combination of possible bioagents of any other of the separate ELISA processes.

13 Claims, 1 Drawing Sheet

Figure 1

COMBINATIONAL STRATEGY FOR IDENTIFICATION OF BIOLOGICAL AGENTS

REFERENCE TO PRIOR APPLICATIONS

Reference is made to U.S. application Ser. No. 09/837,946, filed Apr. 19, 2001, entitled "Automated Computer Controlled Reporter Device for Conducting Immunoassay and Molecular Biology Procedures."

FIELD OF THE INVENTION

This invention relates to detection of bioagents (and/or nucleic acids), and, more particularly, to a method for identifying the presence of bioagents and/or nucleic acids of specific interest in a specimen in the shortest possible time, with a minimum of necessary equipment and using known tests.

BACKGROUND

Health authorities are ever alert to the outbreak of a contagious disease that, if not checked early, could grow to epidemic proportion amongst the general population. To that purpose, the health authorities are charged with monitoring the environment for the incidence of unusual illnesses, symptomatic of a disease, obtain and analyze samples to identify the biological agent causing the disease, and, once identified, publish protective measures that must be taken to halt the spread of the disease. Typically, biological agents, such as virus and bacteria, are part of nature, and outbreaks of disease occur naturally. However, biological terrorism, the deliberate release of a harmful virus or bacteria or other biological agent (hereafter, "bioagent") amongst a general population, and bio-warfare, the deliberate release of a bioagent against military troops in battle, are also of concern.

One known test procedure or process for detection of a specific bioagent that is applicable to a variety of fields, such as biotechnology, environmental protection and public health, is the enzyme linked immunoassay (hereafter referred to as "ELISA"). The ELISA process constitutes an identification process that uses molecular interactions to uniquely identify target substances. A basic definition of ELISA is a quantitative in vitro test for an antibody or antigen (e.g., a bioagent) in which the test material is adsorbed on a surface and exposed to a complex of an enzyme linked to an antibody specific for the substance being tested for with a positive result indicated by a treatment yielding a color in proportion to the amount of antigen or antibody in the test material. The basic ELISA procedure is described more specifically, for one, in a book entitled Methods in Molecular Biology Vol 42, John R. Crowther, Humana Press, 1995.

The "antibody specific for the substance being tested for" in the foregoing definition constitutes a recognition molecule, a molecule that is capable of binding to either reactant or product molecules in a structure-restricted manner. That is, the recognition molecule binds to a specific three-dimensional structure of a molecule or to a two-dimensional surface that is electrically charged and/or hydrophobic in a specific surface pattern. It may also be recognized that ELISA-like approaches using other recognition molecules can also be used, such as aptamers, DNA, RNA and molecular imprint polymers.

More recently, the foregoing definition for ELISA has been expanded beyond the colormetric approach, wherein color and color intensity is used as a reporter or indicia of the antigen or antibody, to include a voltametric or amperiometric approach to detection, wherein a rate of change of voltage or current conductivity in proportion to the amount of antigen or antibody contained in the test material. Patent Cooperation Treaty application PCT/US98/16714, filed Aug. 12, 1998 (International Publication No. WO 99/07870), entitled "Electrochemical Reporter System for Detecting Analytical Immunoassay and Molecular Biology Procedures" (hereafter the "16714 PCT application"), claiming priority of U.S. patent application Ser. Nos. 09/105,538 and 09/105,539"), to which the reader may refer, describes both a colormetric and an electrochemical reporter system for detecting and quantifying enzymes and other bioagents in analytical and clinical applications. The electrochemical reporter system of the 16714 PCT application employs a sensor for detecting voltametric and/or amperiometric signals that are produced in proportion to the concentration of organic (or inorganic) reporter molecules by redox (e.g. reduction-oxidation) recycling at the sensor.

In brief, in the ELISA test, the suspect bioagent is initially placed in a water-based buffer, such as a phosphate buffered saline solution, to form a sample solution. That sample solution is mixed with a quantity of particles, beads, the surface of which is coated with an antibody to the suspect bioagent, a recognition molecule (also sometimes referred to as a receptor molecule). The particular antibodies used to coat the beads are known to bind to the bioagent of interest or of concern and is a primary antibody or "1° Ab". That is, the antibody coating exhibits a chemical "stickiness" that is selective to specific bioagents.

Any bioagent present in the sample solution binds with a non-covalent bond to a respective antibody and thereby becomes attached to a respective one of the beads in the mixture-solution. If the sample solution does not contain a bioagent or if the bioagent that is present in the solution is not one that binds to the selected antibody, then nothing binds to the foregoing antibody. Further processing of the ELISA process then shows nothing.

Assuming the suspect bioagent is present in the sample, the bioagent bonds to the antibody that is coated on the beads. The solution then contains a quantity of bioagent molecules bound respectively to a like quantity of coated beads. The mixture is optionally washed, as example, in a phosphate-buffered saline, and a second antibody, more specifically, an antibody and enzyme linked combination, is then added to the mixture. The second antibody is also one that is known to bind to the suspect bioagent, another recognition molecule. The second antibody may be either be one that is monoclonal, e.g. one that binds to only one specific molecule, or polyclonal, e.g. a mixture of different antibodies each of which shares the characteristic of bonding to the target bioagent. The enzyme, is covalently bound to the second antibody and forms a complex that is referred to as a secondary antibody-enzyme conjugate or "2°Ab-enz". As known by those skilled in the art, an enzyme is a "molecule scissors", a protein that catalyzes a biological reaction, a reaction that does not occur appreciably in the absence of the enzyme. The enzyme is selected to allow the subsequent production of an electrochemically active reporter.

The 2°Ab-enz binds to the exposed surface of the immobilized bioagent to form an "antibody sandwich" with the bioagent forming the middle layer of that sandwich. The antibody sandwich coated beads are washed again to wash away any excess 2°Ab-enz in the solution that remains unbound.

The beads and the attached antibody sandwich, the 1°Ab/bioagent/2°Ab-enz complex, in the solution are placed over the exposed surface of the redox recycling sensor. The substrate of the foregoing enzyme is added to the solution and the substrate is cleaved by the enzyme to produce an electrochemically active reporter. The substrate of the enzyme, referred to as PAP-GP, is any substance that reacts with an enzyme to modify the substrate. The effect of the enzyme is to separate, cut, the PAP, a para-amino phenol, the electrochemically active reporter, from the GP, an electrochemically inactive substance.

The foregoing chemical reaction is concentrated at the surface of the sensor. The rate of production of the foregoing reporter (PAP) is proportional to the initial concentration of bioagent. The reporter reacts at the surface of the sensor, producing an electrical current through the sensor that varies with time and is proportional to the concentration of the bioagent, referred to as redox recycling. The occurrence of the electric current constitutes a positive indication of the presence of the suspect bioagent in the sample. Analysis of the electric currents produced over an interval of time and comparison of the values of that electric current with existing laboratory standards of known bioagents allows quantification of the concentration of bioagent present in the initial sample.

As recognized, the greater the number of laboratories equipped to check for specific bioagents and the more widely those laboratories are dispersed over a geographic region, the more swiftly a bioagent occurring in the environment can be recognized and handled by the health authorities. Unfortunately, the number of such facilities is relatively small. Recognizing that greater dispersal of ELISA test capability among the general population is a desirable goal in bioagent detection, it is also recognized that a lack of trained personnel is problematic, and that wide dispersal of ELISA test capability may not as a practical matter be possible unless the ELISA test can be carried out by persons of lesser skill.

As example, the electrochemical ELISA procedure and apparatus of the cited 16714 PCT application and the predecessor ELISA procedures appear well suited to practice in a microbiology laboratory by highly skilled personnel who are alert to the details of the test process. Other facilities or environments in which such an analysis is desirable, however, may not enjoy either the availability of highly skilled technicians or an adequately equipped laboratory. In such environments, the availability of a foolproof, user-friendly test apparatus that is able to analyze a sample and report a meaningful result with minimal human intervention is certainly desirable.

Recognizing that need, the present inventors, together with other co-inventors, invented an automated test procedure, which is described in U.S. patent application Ser. No. 09/837,946, filed Apr. 19, 2001, entitled Automated Computer Controlled Reporter Device for Conducting Immunoassay and Molecular Biology Procedures (hereafter the "946 application"), assigned to the assignee of the present application, the content of which is incorporated herein by reference. The apparatus of the '946 application provides a user friendly stand-alone portable unit that is able to automatically perform an ELISA test which may be operated by persons who are not biologists and who require minimal training. The automated system contains a number of solutions and pumps that are controlled by a programmed computer.

The foregoing system also employs beads of magnetic material and a magnetic positioning device to manipulate and position the coated magnetic beads under control of the computer, such as during the washing steps of the ELISA process, and in positioning the beads at the sensor during redox recycling. The automated test device of the '946 application provides a solution to dispersal of testing units that takes into account the lesser skills of prospective operators. However, like the prior manual procedure, the automated procedure is unable to determine which suspected virus should be sought or the priority to employ in the search to identify the suspect bioagent.

Each of the foregoing ELISA test procedures, whether manual or automatic, and/or colormetric or amperiometric, searches for a single suspect bioagent, and, if detected, determines the concentration of that bioagent. The identification is essentially a "go" or "no-go" procedure. In one approach to identification, the test procedure is repeated using different receptor molecules until the bioagent is identified. If the result of the one test is a "no go", then a second bioagent is made the suspect and the test is repeated for that second bioagent. The foregoing test procedure may be continued almost indefinitely until the particular bioagent is detected, one exhausts the supply of known receptor molecules or one exhausts the supply of known bioagents.

Even though the ELISA test is automated, as when employing the test apparatus of the cited '946 application, identification of a bioagent could take a great deal of time to accomplish if testing is accomplished in serial order, particularly if the bioagent turns out to be the least likely one in an extended list of suspect bioagents. One solution for reducing the time to identification is to utilize a bank of test apparatus, one test apparatus for each bioagent in the group of possibilities, and carry out the separate ELISA test procedures concurrently. Such an approach requires a great deal of equipment, particularly if one tests for a great number of different bioagents, and appears to be impractical. As example, if one is concerned about fifteen different bioagents as possibilities, it is possible to concurrently test using a bank of fifteen testers or other test apparatus, each catered to a respective bioagent. But so much test apparatus is expensive, requires a great deal of space in total, and takes much effort to maintain. Hence the approach is thought to be impractical.

Accordingly, an object of the present invention is to reduce the number of individual tests that must be performed to identify the presence of one of multiple suspect bioagents in a sample, and to reduce the time required to make such identification.

A further object of the invention is to provide the means to search for bioagents with increased speed and efficiency.

And, a still further object of the invention is define a testing protocol for application of the ELISA process.

SUMMARY OF THE INVENTION

In accordance with the foregoing objects, the existence of any one of up to $2^N-1$ bioagents in a sample is determined and identified by dividing the sample into N parts and performing N separate identification processes (e.g., ELISA), one process for each of the N parts, where N is an integer greater than 1. Each of those N identification processes is assigned a respective group or combination of bioagents to identify that is unique to the respective identification process, with the bioagents of the group or combination being selected from the $2^N-1$ bioagents and with the sum of those bioagents constituting the group or combination being less than $2^N-1$ bioagents.

Each such identification process is capable of identifying any one of a number of bioagents in the group or combination of bioagents assigned for detection to the respective identification process. At least some of the bioagents in the group or combination of bioagents assigned to one identification process are also shared by the group or combination of bioagents that are assigned for identification to at least one other one of the identification processes and each group or combination is assigned a bioagent that is unique to the respective identification process. Each of the N separate identification processes accordingly possess the capability of uniquely identifying a respective single one of the bioagents from the $2^N-1$ bioagents combination that none of the other identification processes is capable of identifying. By use of combinational logic a particular bioagent may be identified.

In one embodiment in which N equals the number two, the number of bioagents that can be detected using two ELISA processes is three. Thus the sample containing one of the bioagents (or none) is parsed in two and separately tested for the bioagents. The one ELISA process being capable of identifying only bioagents A and B and the other ELISA process being capable of identifying only bioagents B and C, whereby the identification of bioagent B, common to both combinations, is shared. Further, the one process is uniquely capable of identifying bioagent A, the other process is uniquely capable of identifying bioagent C. Thus, if both identification processes identify a bioagent, combination logic dictates that the bioagent is B. Otherwise only one of the two identification processes will identify bioagent A or C if present. As an advantage, the new process permits rapid identification of one of several bioagents with fewer than several tests and/or equipment for several tests.

The foregoing and additional objects and advantages of the invention, together with the structure characteristic thereof, which were only briefly summarized in the foregoing passages, will become more apparent to those skilled in the art upon reading the detailed description of a preferred embodiment of the invention, which follows in this specification, taken together with the illustrations thereof presented in the accompanying drawings.

BRIEF DESCRIPTION OF THE DRAWINGS

The FIGURE of the drawing illustrates the new process.

DESCRIPTION OF THE PREFERRED EMBODIMENTS

The description assumes a familiarity with the ELISA process described in the '16714 PCT application and the '946 application, earlier briefly described. A starting point in an ELISA test is to coat receptor molecules on beads. Specifically the beads are coated with receptor (e.g., recognition) molecule that adsorbs a specific antigen (hereafter referred to as a bioagent). Likewise, the ELISA test requires a secondary antibody-enzyme conjugate (e.g., 2°Ab-enz) specific to the bioagent. The ELISA test for that specific bioagent determines both the presence of that agent in the solution, and, if present, the concentration of the agent in the solution. For the present, the sole purpose of the present invention is to identify the presence of a suspect bioagent.

In this description, the letter X1 represents a bead coating that serves as a receptor for a specific bioagent (and may also represent the secondary antibody-enzyme conjugate (e.g., 2°Ab-enz) specific to the bioagent), the latter bioagent being given a corresponding designation AX1. As example, the bead coatings for three agents AX1, AX2 and AX3 are represented as X1, X2 and X3.

To run an ELISA test for the three bioagents in the foregoing example, using a conventional ELISA test procedure, it is necessary to have three separate beads, a first vial with beads coated with receptor molecule X1, another vial of beads coated with X2 and a third vial coated with receptor molecule X3. It is also necessary to have the three separate secondary antibody-enzyme conjugate (e.g., 2°Ab-enz) specific to the bioagent associated with X1, X2 and X3. A given sample is divided into three parts and placed in the corresponding vial of coated beads. Each vial is tested in turn using the ELISA procedure to determine the existence of the corresponding agent in the sample and, if present, the concentration of each.

Alternatively, if one is using the ELISA test to merely determine if any one of bioagents AX1, AX2 and AX3 is present without identifying the one that is present, one could take beads from each of the foregoing three vials and mix the beads together in a single vial to form a single mixture. Then the ELISA test is run on that mixture using the appropriate antibody-enzyme linked combinations for each of the three agents simultaneously. The foregoing may be referred to as a "parallel" test procedure. The foregoing does not identify which agent is present, only that at least one of the three bioagents is present.

Much like the last described procedure, in the new method, the beads are to be given a single test for the presence of two or more bioagents, the number of such agents being dependent upon the total number of possible agents being monitored, as later herein described in greater detail. With the new method, however, the specific bioagent present is determined.

The new method employs a mixture of groups of differently coated beads. As example, to formulate a single mixture of beads that may be tested for the presence of more than one type of bioagent simultaneously such as the three agents in the example earlier given, namely agents AX1, AX2 and AX3, multiple batches of coated beads are prepared, one batch of which is coated with receptor molecules X1, a second batch coated with receptor molecules X2 and a third batch coated with receptor molecules X3. Then, as example, equal portions of each batch are mixed together to form a bead mixture.

As those skilled in the art should recognize, a bead may be coated with a number of different receptor molecules producing an equivalent to the foregoing bead mixture. That is the subject of another less preferred embodiment later herein described.

The foregoing bead mixture (or in the embodiment of a multi-coated bead, the bead) may be represented by a letter and descriptors defining the contents of the mixture, as example, A (X1, X2, X3) or represented in the form of a chart of the bead set, which follows, and the agents AX1, AX2 and AX3 that are to be detected by the test of that bead set. As a further simplification of the description and as a further aid to understanding the invention, the preface AX is omitted from the numerical designation assigned to the bioagent, identifying those bioagents simply as 1, 2 and 3. The descriptors X1, X2, X3 to the bead set, are also omitted, identifying the bead mixture simply by a letter A, since the receptor coatings may be inferred from the identification of the bioagents listed in the following sample chart.

| Bead set | Bioagents to be detected by the bead set | | |
| --- | --- | --- | --- |
| A | 1 | 2 | 3 |

The foregoing chart is presented to assist in understanding the convention used herein to represent and/or describe the elements, and not as a part of the invention, which is next described. A first implementation of the process is to run two separate ELISA tests to monitor for three potential agents (e.g., where N identified in the preceding Summary section equals 2). In the interest of obtaining a result quickly, the tests are performed concurrently using separate apparatus. The test may be accomplished manually or automatically, and may be either one in which the outcome is a change in color of the solution, a change in electrical current, a change in electro-chemical luminescence or any other reporter system known or hereafter created that may be applied to the ELISA process as an improvement. Preferably the testing is accomplished by the automated system of the '946 application, in which case the beads are formed of magnetic material and the outcome is a measurable change in electric current.

Apart from the use of recognition molecules in identification testing, it should be realized that the invention is independent of the specific manner or type of testing used. As example, the foregoing automated ELISA system employs the phenomenon of redox recycling at an electrode for generation of measurable electrical current (e.g. reporting). A more recent measurement technique employs "reduction" instead of redox recycling and may be substituted for the redox recycling function in the automated system without any material effect to the present invention. The reduction technique employs measurement of electro-chemical luminescence using an optical sensor in which electrons are pumped into the solution and specific wavelengths of light are emitted. That emission is measureable and serves as an indicator of the bioagent and the concentration.

Returning to the coated beads used in the identification testing, bead mixture A is coated to be receptive to bioagents 1 and 2 (e.g., A(X1, X2)) and bead mixture B is coated to be receptive to bioagents 2 and 3 (e.g., B(X2, X3)). This is represented as Case I.

CASE I-Two Beads

| Bead set | Bioagents to be detected by the bead set | |
| --- | --- | --- |
| A | 1 | 2 |
| B | 2 | 3 |

| Bioagent | Bead set to which recognition molecule of Bioagent applied |
| --- | --- |
| 1 | A |
| 2 | A + B |
| 3 | B |

Figure 1:
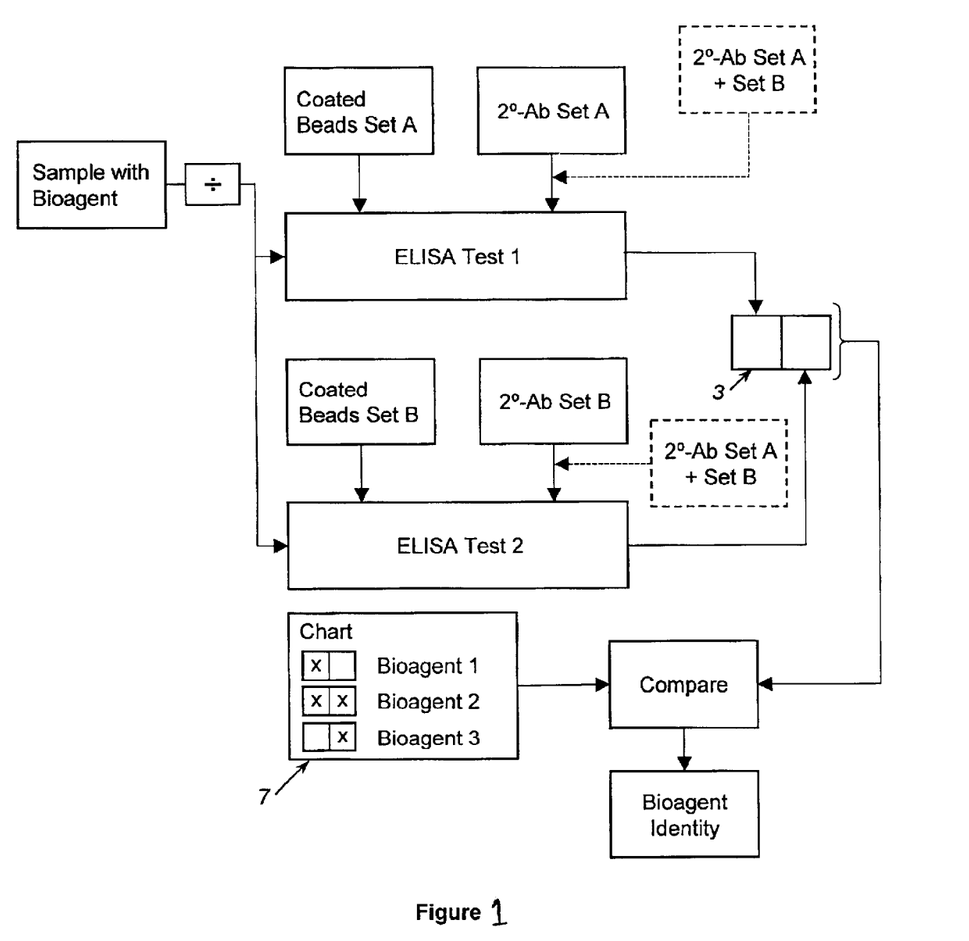

Referring to the figure, the sample 1 that is being tested for a bioagent is parsed into two parts. Half the sample is deposited in the first solution with bead mixture A (set A). The other half is deposited in the second solution with bead mixture B (set B).

Each of the testers contains the respective secondary antibody-enzyme conjugates (e.g., 2°Ab-enz) (set A) for the bioagents in bead mixture A, specifically two different secondary antibody-enzyme conjugates, and the respective secondary antibody-enzyme conjugates (set B) for the bioagents in bead mixture B. Since bead mixture A contains two different receptor molecules for the respective possible two bioagents, the two conjugates will be added to the solution being tested at the appropriate stage of the ELISA test. Likewise bead mixture B contains two different receptor molecules for respective ones of the two different receptor molecules, the two secondary antibody-enzyme conjugates (sometimes referred to as conjugate solutions) for the latter receptor molecules are used in the second tester and will be added to the solution under test at the appropriate test stage.

The foregoing conjugate solutions may be compounded ahead of time and installed in the automated ELISA system, earlier referred to in which the solutions are relatively inaccessible to the user. Initially, when first practicing the process the foregoing conjugates may be added to the solution in equal amounts. However, that is not a requirement to the present invention. With refinement of the process, it is anticipated that some conjugates may be added in lesser amounts than others of the conjugates and still achieve a satisfactory result.

As in the case of the bead coatings, one of the conjugates is used in both bead mixtures A and B. One ELISA test is run on the first test solution (ELISA test 1) and the second test (ELISA test 2) is concurrently run on the second test solution. The results of the two tests are observed 3, and, in a sense, constitutes a two place code, either 10, 11, or 01. It should be understood that a "1" means "not 0" and that the test result can be quantitative, having possible values between 0 and 1, in addition to being qualitative, having only 0 and 1 as possible values.

If none of the three suspect bioagents is present in the sample under test, then the result of both tests is negative (e.g., 00). If bioagent AX1 is present, only the first solution produces a positive indication in the test (e.g., 10). If bioagent AX3 is present, only the second solution produces a positive indication in the other test (e.g., 01). If bioagent AX2 is present, then both tests produce a positive indication (e.g., 11). The positive or negative indication of the combination of the two testers provides unique information, a kind of code. For convenience a chart 7 may be constructed containing the various results possible and correlating each possible result to a specific bioagent. Thus, one is able to use two tests to determine the existence of any of the three kinds of bioagents if only a single one of the three bioagents being sought is present in the sample.

The foregoing testing is accomplished in parallel, employing two test apparatus to determine the result in the shortest possible time. In the prior art procedure, the test for each bioagent is undertaken separately. To determine the result in the shortest possible time using the prior art procedure, three testers are necessary to carry out the testing concurrently. The foregoing testing using the described combinational logic can be accomplished with a single tester, but, because two separate tests are required, that would double the time needed to determine the result. In keeping with the purpose of rapid identification, concurrent testing in separate test apparatus is preferred. Thus, the object of the invention is achieved.

The foregoing test could produce an ambiguity if multiple bioagents are present together in the sample. As example, if the pair of tests of beads A and B both return a positive indication then only bioagent 2 should be present. However, in the presence of two bioagents in the sample, the indication could also mean that both bioagents 1 and 3 are simultaneously present in the tested sample, and not bioagent 2. Although occurrence of multiple bioagents seems implausible and may be disregarded, some extra testing may be desirable in certain circumstances to resolve or eliminate that possibility.

To resolve the foregoing ambiguity, a third test must be then run to determine if bioagent 2 is present. That third test must be performed using the prior ELISA test procedure. As recalled one of the bead mixtures was compounded from individual vials of coated beads in which the beads in a vial each contained a receptor molecule for a single bioagent. Hence, a set of beads containing only the receptor molecule for bioagent AX2 should be on hand. That set is mixed in solution with another portion of the sample, the ELISA test is run on the solution and the presence of bioagent AX2 determined or not from the test. If the test proves negative, then one may conclude that multiple bioagents, AX1 and AX3, are present in the sample. The latter fact may be reconfirmed by running separate ELISA tests for each of bioagents AX1 and/or AX3.

The foregoing ELISA test for bioagent AX2 may employ the same two secondary antibody-enzyme conjugates for the bioagents AX1 and AX2 that was used in the initial test, earlier described. Since in this test to resolve the ambiguity the bead is coated with receptor molecules for only bioagent AX2, the secondary antibody-enzyme conjugates for bioagent AX1 in the ELISA test will have no effect.

To minimize the possibility of an ambiguity, in practical application the biologist responsible for the testing should exercise judgement in grouping the suspect bioagents, if possible. Based on experience or information, the biologist or other test operator should decide which of the three agents being monitored is the least likely to occur. A particular bioagent may be less likely to occur because of the relative greater difficulty in handling, releasing and/or dispersing a particular bioagent into the environment, or because the one bioagent is much more rare than the others, or on any other sound basis. And, after having determined which agent is the most rare of the three bioagents, the biologist should assign that bioagent as bioagent AX2 in the formulation of the foregoing pair of tests. That, is using the rarest bioagent as the one for which the corresponding receptor molecules are coated on half of the beads comprising bead set A and half of the beads comprising bead set B.

A greater number of possible bioagents may be identified by the addition of a third bead and an additional test (or tester). The foregoing testing process may be enlarged in scope by adding another bead (or bead mixture) C. By treating bead mixture A to be responsive to bioagents 1, 2, 5 and 7, treating bead (or bead mixture) B to be responsive to bioagents 2, 3, 4 and 7, and treating bead mixture C to be responsive to bioagents 4, 5, 6 and 7, the presence of seven possible bioagents may be individually identified. An eighth case is that no bioagent is present.

The respective testers will include the secondary antibody-enzyme conjugates for each of the same bioagents being sought by the respective tester. As example the tester (or test) in which bead mixture A is used, will include the secondary antibody-enzyme conjugates for bioagents 1, 2, 5 and 7. The latter conjugates are added, as example, in equal amount to the test solution during the appropriate phase of the test. To save time the three sets of beads may be tested in three respective testers, preferably concurrently, to determine the presence any one of seven separate bioagents, a savings in equipment compared to the seven separate testers required by the prior art procedures to perform the tests in the same amount of time. The foregoing is represented in the following charts.

CASE II-Three beads.

| Bead set | Bioagents to be detected by the bead set | | | |
|---|---|---|---|---|
| A | 1 | 2 | 5 | 7 |
| B | 2 | 3 | 4 | 7 |
| C | 4 | 5 | 6 | 7 |

| Bioagent | Bead set to which recognition molecule of Bioagent applied |
|---|---|
| 0 | |
| 1 | A |
| 2 | A + B |
| 3 | B |
| 4 | B + C |
| 5 | A + C |
| 6 | C |
| 7 | A + B + C |

In like manner, by the addition of a fourth bead (or bead set) and using four ELISA testers or tests concurrently it is possible to identify any of fifteen possible bioagents on a sample in a minimum of time. The sample containing the suspect bioagent is divided into four parts, one for each of the four testers. The coating of each bead set (and, inferentially, the corresponding secondary antibody-enzyme conjugate for the respective test) is described by the chart labeled CASE III, which follows.

CASE III-four beads.

| Bead set | Bioagents to be detected by the bead set | | | | | | | |
|---|---|---|---|---|---|---|---|---|
| A | 1 | 2 | 5 | 7 | 10 | 12 | 13 | 14 |
| B | 2 | 3 | 4 | 8 | 10 | 11 | 13 | 14 |
| C | 4 | 5 | 6 | 15 | 10 | 11 | 12 | 14 |
| D | 6 | 7 | 8 | 9 | 11 | 12 | 13 | 14 |

| Bioagent | Bead set to which recognition molecule of Bioagent applied |
|---|---|
| 1 | A |
| 2 | A + B |
| 3 | B |
| 4 | B + C |
| 5 | A + C |
| 6 | C + D |
| 7 | A + D |
| 8 | B + D |
| 9 | D |
| 10 | A + B + C |
| 11 | B + C + D |
| 12 | A + C + D |
| 13 | A + B + D |
| 14 | A + B + C + D |
| 15 | C |

The testing procedure may be further enlarged. With five bead sets, A, B, C, D and E, and five testers, it can be seen that one is able to probe for any of thirty-one (31) different bioagents in a sample.

Generalizing on the foregoing combinations and borrowing from mathematics, the total number, T, of possible combinations of N items, taken successively 1, 2, 3 . . . N items at a time is the integer 2 raised to the Nth power minus one. That is, $T=(2^N-1)$.

As the foregoing equation implies, the number of agents detected can be increased mathematically even further to greater numbers. There is a practical limit to the method, however. That limit depends on the sensitivity of the measurement equipment, the sensitivity of the measurement equipment to detect color during redox recycling, when colormetric testing is used in the ELISA process, or the sensitivity of the measurement equipment to detect current and/or voltage during redox recycling when amperometric detection is used in the ELISA process. As one appreciates, when the volume of a test solution is divided amongst fifteen different conjugates as in Case III, the redox recyling for any one of the individual bioagents, when sensed, is much smaller, than when a volume of test solution is divided amongst only two conjugates as in Case I. At the present the limit to the sensitivity is believed to be thirty-one bioagents or approximately five to ten agents per reaction. However, as the technology of measurement apparatus improves in the future that limit number may be increased further.

In retrospect it is seen that the particular bioagents that are to be detected by a bead set in any of the three cases I, II and III described, and, hence, the recognition molecules that are coated on the beads of each bead set forms a collection or, as variously termed, combination of known bioagents that are to be sought out and detected in running the ELISA test on the respective bead set. It is also seen that such combination or collection of any one bead set is unique in respect of the collection or combination associated with any other coated bead set in the particular identification scheme. As example, in Case III earlier considered, using bead set A, any of known bioagents 1, 2, 5, 7, 10, 12, 13 and 14, defining a collection or combination, may be detected in the associated ELISA procedure. That combination or collection differs from the collection associated with bead set B, which is for detection of known bioagents 2, 3, 4, 8, 10, 11, 13 and 14. Although both of the foregoing collections share detection of bioagent 2 as part of the collection, the collections are unique, notwithstanding the fact that one or more elements or components of the collection being common to another collection. It is also seen that all of the collections are smaller in size than the total number of bioagents that are possible of detection, $2^N-1$, which in Case III equates to fifteen. And, although each of the separate ELISA tests of the associated bead that defines an individual collection of known bioagents is useful to detect the existence of a known bioagent in the sample, actual identification of a particular bioagent, when the presence is detected by one or more of the separate ELISA tests, requires examination of the positive and/or negative results of all of the ELISA tests.

The possibility of multiple bioagents being present was described for Case I in the preceding discussion, and, if suspected, required additional tests to confirm or exclude that possibility. The possibility of multiple bioagents would also exist in the more comprehensive cases, such as Case II, Case III and beyond, and would also require additional testing. Once the results of a test are obtained, should the particular bioagent be one which is identified by two or more of the ELISA tests, then one must test for the alternative bioagents separately for additional bioagents. The particular tests necessary is evident from the foregoing charts. Notwithstanding such additional testing, the amount of testing required would appear to be less than the number required by using the conventional ELISA procedures.

As one appreciates the foregoing method reduces the amount of equipment necessary to run ELISA tests. Generally, the amount of hardware required scales as the log base 2 of the number of bioagents, instead of linearly as in the case of one test/reaction-one bioagent systems.

It should also be understood from the foregoing discussion that the number of different bioagents that may be detected in the plural ("N") concurrent tests is a maximum number, as example, three in Case I, seven in Case II, fifteen in Case III and so on are maximum numbers of bioagents. Therefore, it is always possible to actually test for a lesser number of different bioagents, even though the particular testing arrangement being used is capable of testing for a greater number of different bioagents. As example, the apparatus used for Case III is capable of identifying fifteen different bioagents. If, however, one is only interested in twelve bioagents (more than possible for the apparatus of Case II), one need only prepare and use the receptor molecules (and the corresponding enzyme linked receptor molecules) for those twelve bioagents. The method of Case III would be followed, employing the four ELISA tests and the receptor molecules distributed and used amongst those four tests.

In the foregoing embodiment, a mixture of beads was used to provide the receptor molecules for a number of different bioagents. It is also possible to coat a single bead with receptor molecules for many different bioagents and to run the ELISA process as in the prior embodiment. As example, considering the initial case given of determining the existence of any of three possible bioagents in a sample in a single ELISA process, the test for the presence and identification of any of bioagents AX1, AX2 and AX3 (alternately identified in the chart as bioagents 1, 2 and 3) could be run on a single vial of beads, A, in which all the beads in the vial are all coated with three receptor molecules X1, X2 and X3 for bioagents 1, 2 and 3.

Consider further Case I, earlier discussed, in which any of three bioagents 1, 2, and 3 are to be detected and identified using two ELISA tests that are run in parallel for which bead mixtures A and B were used. Bead mixture A was coated with receptor molecules for bioagents 1 and 2; and that mixture was formed by mixing beads from two separate vials, one of which contained the receptor molecules for bioagent 1 and the other of which contained the receptor molecules of bioagent 2. By coating all the beads with both receptor molecules to form A, only a single vial of beads needs to be maintained. The same holds true for the beads that form mixture B. The two receptor molecules for bioagents 2 and 3 may be coated on all the beads that define B, and only a single vial of beads needs to be maintained.

The ELISA test operates on the foregoing beads in the same manner, and obtains the same result as earlier described for the mixture of beads, which need not be repeated. When one of the three bioagents is present in the sample, bead A tests positive if bioagent 1 is present, bead B tests positive if bioagent 3 is present and both beads A and B test positive if bioagent 2 is present. As is clear from an understanding of the description of the invention, the foregoing alternative is equivalent to the procedure earlier described and falls within the scope of the present invention. It should thus be recognized that the term "bead mixture" and "beads" should be interpreted as being synonymous in the claims that follow, unless the context requires separate meaning.

As recalled from the prior discussion of that ambiguity when both beads A and B test positive that should indicate the presence of bioagent 2, but could also be interpreted to indicate instead that both bioagents 1 and 3 are present. There is a need to separately check for bioagent 2. However, bead A contains receptor molecules for both bioagents 1 and 2. And the conjugate solution in the prior ELISA test (described for the bead mixture) contains the conjugates for both bioagents 1 and 2. A positive indication from the test could not distinguish between bioagents 1 and 2. Thus, it is necessary to maintain separate vials of conjugates for each of bioagents 1 and 2.

By switching the conjugate solution in the ELISA test to that conjugate solely for bioagent 2, the multi-coated bead A may then be tested for the presence of bioagent 2. A positive indication can only mean the presence of bioagent 2. The foregoing alternative embodiment is seen to require storage, handling and change the vials of conjugate solutions in ELISA testing in contrast to changing the beads as is done in resolving the ambiguity as earlier described for the bead mixture.

It may be desirable to reduce the number of conjugate solutions required for conducting the separate ELISA processes of the portions of the sample to minimize maintenance requirements and stock keeping of supplies. Such a reduction is possible when using a bead mixture with the only apparent drawback being a reduction of detection sensitivity. Referring again to the figure of the drawing and Case I (e.g., N equals 2) earlier described, for this additional embodiment the conjugate solutions for set A of the coated beads in ELISA test 1, shown in the box labeled 2°-Ab set A, are replaced by the conjugate solutions for the receptor molecules used on both sets of coated beads A and B, shown in the dash line box labeled 2°-Ab set A+ set B. Further, in ELISA test 2 the conjugate solutions for set B of the coated beads, shown in the box labeled 2°-Ab set B are also replaced by the conjugate solutions in the dash line box labeled 2°-Ab set A+ set B containing conjugate solutions for the receptor molecules used on both sets of coated beads A and B.

In the running of ELISA test 1 on the sample, the individual receptor (2°Ab-enz) molecules of the conjugate solutions are able to bind only to the same bioagent molecules to which the coated beads in bead set A are able to bind. In Case 1, bead set A is able to bind only to bioagents 1 and 2, whereas the receptor molecules in the new conjugate solution are able to bind to bioagents 1, 2 and 3. However, since there is no coated bead to which the conjugate solution component for bioagent 3 is able to bind, nothing can happen, and that component of the conjugate solution is essentially neutral. The remaining components of the solution, the components for bioagents 1 and 2 react just as the components reacted in Case I. The additional component (or, in the case of Cases II and III, components) of the conjugate solution are essentially surplus. The same effect occurs in the running of ELISA test 2. In the latter test the component of the conjugate solution that is unique to bioagent 1 is surplus, since the beads are coated with receptor molecules only for bioagents 2 and 3 and, the remaining components of the conjugate solution that are unique to bioagents 2 and 3 react just as those components reacted in Case I earlier described.

As one appreciates, in such an embodiment one is able to compound a single conjugate solution for use in all of the ELISA tests performed on a sample. The savings of time and stock keeping becomes more significant in the additional cases in which three, four or more ELISA tests are run concurrently, in which circumstance the conjugate solution can contain as many as fifteen, thirty-one or more components, respectively. Adopting the technique is particularly attractive when employing the Automated ELISA apparatus of the earlier cited '946 application, which makes the apparatus described therein easier for unskilled persons to use and maintain.

It is also possible to resolve ambiguities resulting from the presence of multiple bioagents in a sample with the latter embodiment, provided a separate supply of the individual bead components of each bead set is maintained. In that way separate tests may be run for an individual bioagent associated with a particular bead. One may refer to the prior discussions in respect of the resolution of ambiguities, which is not repeated in detail. The only apparent drawback to the inclusion of surplus components in the conjugate solution is that the volume of the useful components in that solution is reduced, and the ELISA test becomes less sensitive.

As those skilled in the art recognize from an understanding of the foregoing, if the last described embodiment is combined with the embodiment that employs multi-coated beads, earlier described, to form still another embodiment of the method, then it would not be possible to resolve ambiguities occurring from the existence of multiple bioagents. Thus, due to the absence of that capability the last named combination is not a preferred one.

The ELISA process is recognized as an identification process that is or can be applied in many different fields, not only to identify bioagents, but nucleic acids as well. However, lacking terminology that is generic to and/or encompasses both bioagents and nucleic acids, it should be understood that the reference to bioagents used herein and in the claims that follow in this application includes nucleic acids. Further, identification processes equivalent to ELISA may be developed that use other recognition molecules, such as aptamers, DNA, RNA and molecular imprint polymers, and, hence, are ELISA-like in nature. The method described herein may be employed for those procedures. Thus for the purposes of this invention, the term ELISA should be construed to encompass all such ELISA-like procedures.

It is believed that the foregoing description of the preferred embodiments of the invention is sufficient in detail to enable one skilled in the art to make and use the invention without undue experimentation. However, it is expressly understood that the detail of the elements comprising the embodiment presented for the foregoing purpose is not intended to limit the scope of the invention in any way, in as much as equivalents to those elements and other modifications thereof, all of which come within the scope of the invention, will become apparent to those skilled in the art upon reading this specification. Thus, the invention is to be broadly construed within the full scope of the appended claims.

What is claimed is:

1. A method of determining the existence of and identifying any one of a plurality of $2^N-1$ different bioagents in a sample containing a bioagent of said plurality of $2^N1$ different bioagents, where N is an integer greater than 1, comprising the steps of:

dividing the sample into N parts; and performing a separate detection process on each of the N parts of the sample to define a plurality of N detection processes, each of said N detection processes employing molecular interactions to uniquely identify bioagents, each of said separate detection processes of said plurality of N detection processes for detecting the presence of any bioagent within a defined collection of bioagents found within said plurality of $2^N-1$ different bioagents, said defined collection of bioagents detected by any one of said separate detection processes in said plurality of N detection processes being different from the collection of bioagents that is detected by any other of said separate detection processes in said plurality of N detection processes; said collections of bioagents in total including said entire plurality of $2^N-1$ different bioagents, and wherein a collective result of said plurality of N detection processes identifies an individual one of said plurality of $2^N-1$ bioagents.

2. The method of determining the existence of and identifying any one of a plurality of $2^N-1$ different bioagents in a sample containing a bioagent of said plurality of $2^N-1$ different bioagents as defined in claim 1, wherein each of said plurality of N detection processes comprises an enzyme linked immunoassay ("ELISA") process.

3. The method of determining the existence of and identifying any one of a plurality of $2^N-1$ different bioagents in a sample containing a bioagent of said plurality of $2^N-1$ different bioagents as defined in claim 2, wherein said integer is 2.

4. The method of determining the existence of and identifying any one of a plurality of $2^N-1$ different bioagents in a sample containing a bioagent of said plurality of $2^N-1$ different bioagents as defined in claim 2, wherein said integer is 3.

5. The method of determining the existence of and identifying any one of a plurality of $2^N-1$ different bioagents in a sample containing a bioagent of said plurality of $2^N-1$ different bioagents as defined in claim 2, wherein said integer is 4.

6. The method of determining the existence of and identifying any one of a plurality of $2^N-1$ different bioagents in a sample containing a bioagent of said plurality of $2^N-1$ different bioagents as defined in claim 2, wherein said integer is 5.

7. A method of determining the existence of and identifying any one of a plurality of $2^N-1$ different bioagents in a sample containing a bioagent of said plurality of $2^N-1$ different bioagents, where N is an integer greater than 1, comprising the steps of:
    dividing the sample into N Darts; and
    performing a separate detection process on each of the N parts of the sample to define a plurality of N detection processes, each of said N detection processes employing molecular interactions to uniquely identify bioagents, each of said separate detection processes of said plurality of N detection processes for detecting the presence of any bioagent within a defined collection of bioagents found within said plurality of $2^N-1$ different bioagents, said defined collection of bioagents detected by any one of said separate detection processes in said plurality of N detection processes being different from the collection of bioagents that is detected by any other of said separate detection processes in said plurality of N detection processes; said collections of bioagents in total including said entire plurality of $2^N-1$ different bioagents, and wherein the collective result of said plurality of N detection processes identifies an individual one of said plurality of $2^N-1$ bioagents, said step of performing said separate identification process on each of said N parts includes the steps of:
        coating beads in N different collections and coating each collection of beads in said N different collections with receptor molecules for less than said $2^N-1$ different bioagents but in which said N different collections contain collectively receptor molecules for all of said $2^N-1$ multiple bioagents, with one of said receptor molecules in each of said collections being a receptor for the same bioagent, and with another of said receptor molecules in each of said collections being unique amongst the receptor molecules contained in all other of said collections; and
        applying each collection of coated beads in a respective one of said separate identification processes.

8. The method of determining the existence of and identifying any one of a plurality of $2^N-1$ different bioagents in a sample containing a bioagent of said plurality of $2^N-1$ different bioagents as defined in claim 2, wherein said step of performing said separate ELISA process on each of said N parts includes the steps of:
    coating beads in N different collections and coating each collection of beads in said N different collections with receptor molecules for less than said $2^N-1$ multiple bioagents but in which said N different collections contain collectively receptor molecules for all of said $2^N-1$ multiple bioagents, with one of said receptor molecules in each collection being a receptor for the same bioagent, and with another of said receptor molecules in each of said collections being unique amongst the receptor molecules contained in all other of said collections; and
    applying each collection of coated beads in a respective one of said separate ELISA processes.

9. The method of determining the existence of and identifying any one of a plurality of $2^N-1$ different bioagents in a sample containing a bioagent of said plurality of $2^N-1$ different bioagents as defined in claim 8, wherein said step of coating each collection of beads in said N different collections with receptor molecules for less than said $2^N-1$ multiple bioagents, includes the step of:
    coating individual groups of beads with receptor molecules for individual bioagents of said collection and mixing said groups together to form a collection of beads containing receptor molecules for the bioagents in said collection.

10. The method of determining the existence of and identifying any one of a plurality of $2^N-1$ different bioagents in a sample containing a bioagent of said plurality of $2^N-1$ different bioagents as defined in claim 8, wherein said step of coating each collection of beads in said N different collections with receptor molecules for less than $2^N-1$ multiple bioagents, includes the step of:
    coating beads with receptor molecules for the bioagents of said collection.

11. The method of determining the existence of and identifying any one of a plurality of $2^N-1$ different bioagents in a sample containing a bioagent of said plurality of $2^N-1$ different bioagents as defined in claim 8, includes the step of:
    compounding a conjugate solution for said ELISA process in which said conjugate solution contains secondary antibody-enzyme conjugate ("2°Ab-Enz") molecules for at least each of the bioagents in said collection.

12. The method of determining the existence of and identifying any one of a plurality of $2^N-1$ bioagents in a sample containing a bioagent of said plurality of $2^N-1$ different bioagents as defined in claim 1 further comprising the step of comparing the results of the tests with a chart, said chart correlating the test results of the N detection processes to specific bioagents, and determining the bioagent identified by said chart.

13. A method of determining the existence of and identifying any one of a plurality of $2^N-1$ different bioagents in a sample containing a single bioagent, where N is a number selected from the series of integers comprising 2, 3, 4, 5 . . . x, comprising the steps of:
    dividing said sample into N parts;
    distributing said sample amongst N separate ELISA processes; and
    performing a separate enzyme linked immunoassay ("ELISA") process on each of N parts to produce N results, each of said N results constituting either an affirmative or negative indication of the presence of one of said plurality of different bioagents in a respective one of said N parts of said sample wherein said N results collectively serve to identify the bioagent contained in said sample; each of said N separate ELISA processes being associated with a pre-defined collection of said plurality of $2^N-1$ different bioagents for detecting the presence in a sample of any one bioagent of said associated predefined collection of said plurality of $2^N-1$ different bioagents, the collection of said plurality of $2^N-1$ different bioagents associated with any one of said N separate ELISA processes being different from the collection of said plurality of $2^N-1$ different bioagents associated with any other one of said N separate ELISA processes; and analyzing said N results to identify the bioagent in said sample;

said step of performing a separate enzyme linked immunoassay ("ELISA") process on each of said N parts of said sample, including the steps of:

coating beads in N different groups and coating each group of beads in said N different groups with receptor molecules for a predefined collection of bioagents, said collection of bioagents constituting less than said plurality of $2^N-1$ different bioagents but in which said N different groups collectively contain receptor molecules for all of said plurality of $2^N-1$ different bioagents, with one of said receptor molecules in each said group being a receptor for the same bioagent, and with another of said receptor molecules in each said group being unique amongst the receptor molecules of all other of said N different groups;

xxxx make a dependent claim by modifying the coating of a "group"

compounding a conjugate solution for each said in which said conjugate solution contains secondary antibody-enzyme conjugate (2°Ab-Enz) molecules for at least each of the bioagents in said predefined collection; and applying each of said N groups of coated beads in a respective one of said separate ELISA processes.

* * * * *

UNITED STATES PATENT AND TRADEMARK OFFICE
CERTIFICATE OF CORRECTION

PATENT NO. : 6,803,202 B2
DATED : October 12, 2004
INVENTOR(S) : Brian M. Sullivan and Denes L. Zsolnay It is certified that error appears in the above-identified patent and that said Letters Patent is hereby corrected as shown below:

<u>Column 18,</u>
Lines 11 and 12, delete "xxxx make a dependent claim by modifying the coating of a "group";
Line 13, "for each said in" should read -- for each said ELISA process in --.

Signed and Sealed this

Twenty-second Day of March, 2005

JON W. DUDAS
*Director of the United States Patent and Trademark Office*